United States Patent
Rella

[11] 4,105,035
[45] Aug. 8, 1978

[54] NASAL PROSTHESIS
[76] Inventor: Agnus Rella, c/o Pesce 160-67 23 Ave., Whitestone, N.Y. 11357
[21] Appl. No.: 742,627
[22] Filed: Nov. 17, 1976
[51] Int. Cl.² .......................................... A61M 29/00
[52] U.S. Cl. ................................................. 128/342
[58] Field of Search .................. 128/76 R, 76 C, 342, 128/89, 83, 343

[56] References Cited
U.S. PATENT DOCUMENTS 1,481,581  1/1924  Woodward ........................ 128/342
2,010,485  8/1935  Heath ................................... 128/342
2,335,936  12/1943  Hanlon ................................ 128/342

Primary Examiner—John D. Yasko

[57] ABSTRACT

Prosthesis apparatus for inserting within the nose to alleviate breathing created by a deviated septum comprising a trapizoid like structure composed of a pair of elongated members and transverse member with apertures in said members for free air flow in the nasal chamber, the said structure being flexible and disposed to gradually shift said deviated septum over a time period.

3 Claims, 5 Drawing Figures

NASAL PROSTHESIS

One of the basic flaws in the human anatomy is the one that concerns itself with the deviated septum, and in particular that deviation in the nasal bone which inherently blocks the air-passages in such a way as to impede the free flow of air through the nostrils during the breathing process.

Because there is blockage of air thru its nostrils, stagnation creates considerable discomfort to the person and permits an environment which leads to infection, post-nasal drip, and affects the speech patterns of the person that requires improvement.

It is therefore a principal object of the invention to provide apparatus which improves breathing for persons having deviated septums and thereby improves their well-being.

A still further object of the invention is to provide apparatus for persons having deviated septums that permits free-flow of air through such nostrils, alleviates or reduces infection and post-nasal drip and improves speech patterns and the overall being of a person, Further objects and advantages will become apparent from a reading of the specifications and a study of accompanying drawings.

Figure 1:
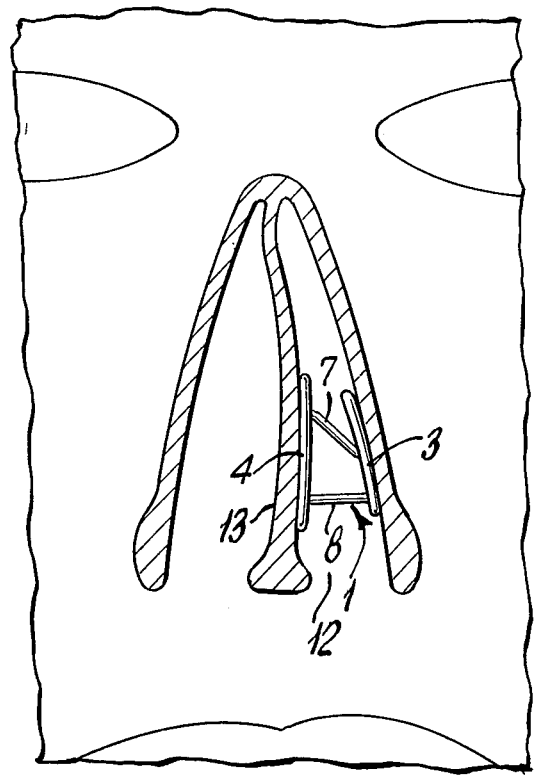
FIG. 1 shows in pictorial form a typical nostril with deviated septum and prosthesis apparatus therein according to one embodiment of the invention.
Figure 3:
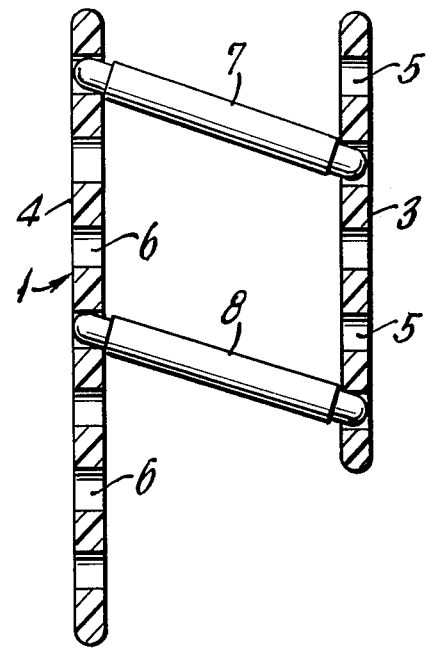
FIG. 3 is a section through the line 3–3 of FIG. 2.
Figure 2:
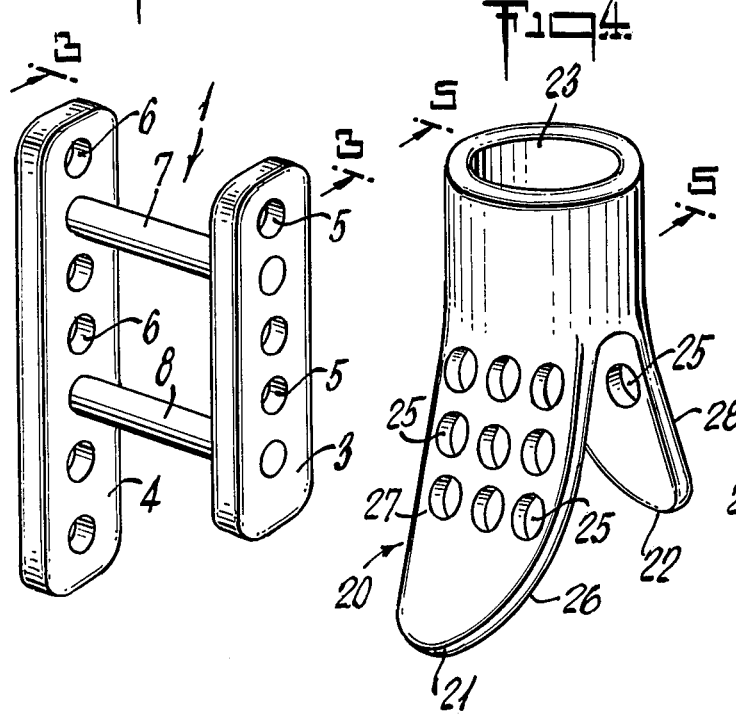
FIG. 2 shows structurally or perspective view of nasal prosthesis according to the invention.

Now describing the invention with particularity according to the various drawings and referring in particular to FIGS. 1 - 3, there is shown therein a nasal prosthesis 1, having a tropazoidal configuration whose elongated sides 3, 4 have a plurality of spaced apart perforations 5 disposed to permit the free flow of air there through or to create an alternate air passage when the prosthesis is functionally operative. The elongated sides 3, 4 are held structurally by transverse cross-beams 7, 8 and disposed to permit the distension of sides 3, 4 when the prosthesis is inserted within the nostrils passageway 10 or shown in FIG. 1. The prosthesis member has one of its elongated sides 4 further extended than side 3 to permit easy manipulation within and without the nasal passageway. It may be appreciated that these prosthesis 1 as shown in the respective figures is made of any reliable pliable material such as plastic and the like.

In FIG. 1 it can be seen that the prosthesis 1 is inserted within the nasal passage 12 in a manner to cause the deviated septum membrane 13 to give thereby giving the passageway 12 a larger opening to permit a freer flow of air.

The apertures or perforations 5 permits air circulation and suitable drainage not otherwise conveniently available. The penetration of the prosthesis member into the passageway is a function of relief desired and time or duration of position. It is appreciated that the use of the prosthesis is a gradual one and must be used over a period of time in accordance with the comfort of the user. The user causes increased penetration over a time period commensurate with his capability of withstanding discomfort and increased need.

Figure 4:
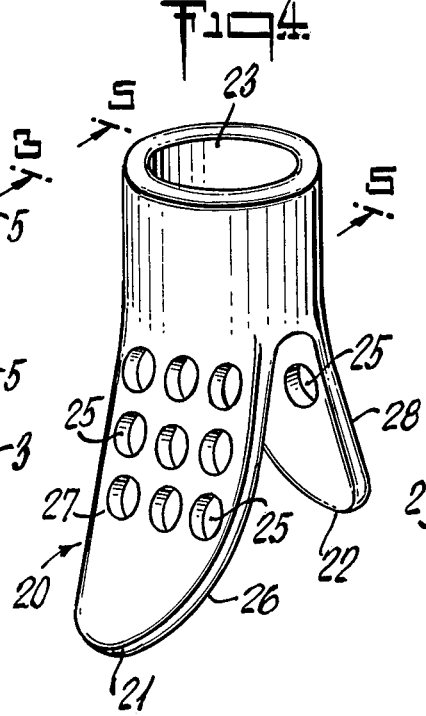
FIG. 4 shows in perspective a nasal prosthesis according to another embodiment of the invention.
Figure 5:
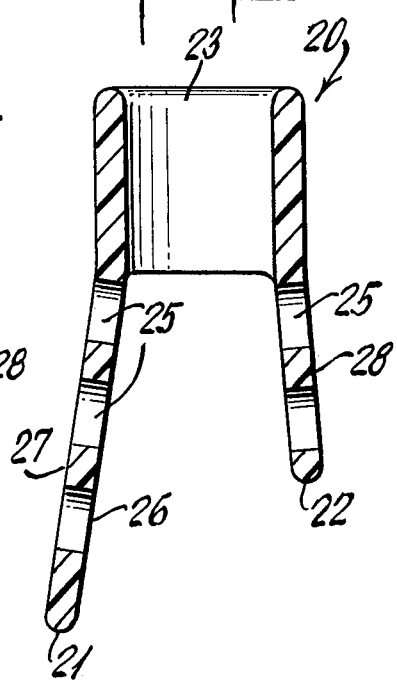
FIG. 5 is a section through the line 5–5 of FIG. 4.

FIGS. 4 and 5 show another configuration representing a further embodiment of its invention. In particular the prosthesis 20 comprises a pair of elongated sides 21, 22 separated and structurally held together by a central cylindrical piece 23, the elongated sides having a plurality of spaced apart apertures 25 both vertically and horizontally for purposes of air access in FIGS. 2, 3. This particular configuration includes an elongated extension 26 of side 27 as opposed to side 28. Further the structure is pliable and disposed to constrict when functionally operable.

The foregoing description related to the various embodiments are for the purpose of describing the invention with a certain particularity but that it may be understood other modes and structural elements may be used without detracting from the true purpose and intent of the invention which is to provide apparatus which alleviates and permits free and comfortable breathing for those having abnormal deviated septums.

Having described the invention what is claimed is:

1. Prosthesis nasal apparatus for alleviating breathing constraints comprising
   (a) a pair of elongated pliable spaced apart shiftable means relative to each other,
   (b) a pair of transverse pliable structural means attached to said elongated shiftable means and shiftable therewith to comprise a single flexible structure, and
   (c) through spaced apart apertures on said elongated structural means for permitting free air flow when the said structure is inserted within the nasal passgeway and also permitting adjustments of the said sides relative to each other over a period of time commensurate with the users capability of withstanding discomfort and need.

2. Prosthesis nasal apparatus as per claim 1 and wherein said elongated means includes elongated structural members one of which includes a further extension for purposes of manipulating the structure within and without the nose.

3. Prosthesis nasal apparatus as per claim 1 and wherein said transverse means includes a cylindrical member whose outer periphery is attached to depending elongated structural means comprising the prosthesis apparatus.

* * * * *